United States Patent [19]

Per-Lee et al.

[11] Patent Number: 5,673,455
[45] Date of Patent: Oct. 7, 1997

[54] APPLICATOR DEVICE WITH SCREW-ON ATTACHMENTS

[76] Inventors: Myra S. Per-Lee, 16136 Avenida Venusto, #2, San Diego, Calif. 92128; Florentino Cabais, 15620 Smoke Tree Ave., Hesperia, Calif. 92345

[21] Appl. No.: 398,892

[22] Filed: Mar. 6, 1995

Related U.S. Application Data

[63] Continuation-in-part of Ser. No. 308,642, Sep. 19, 1994, Pat. No. 5,437,372, which is a continuation of Ser. No. 107,510, Aug. 17, 1993, Pat. No. 5,388,700.

[51] Int. Cl.$^6$ ............................................. A47K 7/02
[52] U.S. Cl. ................... 15/210.1; 15/105; 15/145; 15/229.11; 15/244.3; 601/137
[58] Field of Search ..................... 15/244.1, 244.2, 15/244.3, 209.1, 210.1, 105, 143.1, 145, 229.11; 601/136, 137, 138, 17

[56] References Cited

U.S. PATENT DOCUMENTS

| | | | |
|---|---|---|---|
| 455,567 | 7/1891 | Kraft | 15/244.1 |
| 719,596 | 2/1903 | Lauterbach | 15/244.1 |
| 2,491,274 | 12/1949 | McNeill | 15/244.1 |
| 2,719,315 | 10/1955 | Sheehan | 15/210.1 |
| 2,736,913 | 3/1956 | Mirth | 15/122 |
| 3,568,237 | 3/1971 | Rhodes | 15/244 |
| 3,955,233 | 5/1976 | Nakamura | 132/320 X |
| 4,032,239 | 6/1977 | Maupin | 15/228 X |
| 4,176,420 | 12/1979 | Magid | 15/230 |
| 4,184,221 | 1/1980 | Edwards | 15/114 |
| 4,299,005 | 11/1981 | Brown | 15/244 |
| 4,381,766 | 5/1983 | Avolio | 15/210.1 X |
| 4,475,836 | 10/1984 | Colognori | 401/201 |
| 4,615,066 | 10/1986 | Colognori | 15/244 |
| 4,934,011 | 6/1990 | Haug | 15/145 |
| 5,003,659 | 4/1991 | Paepke | 15/244.1 X |
| 5,052,840 | 10/1991 | St. Cyer | 15/244.1 |
| 5,123,431 | 6/1992 | Wilson | 132/320 |
| 5,240,339 | 8/1993 | De Forest et al. | 15/244.2 |
| 5,402,550 | 4/1995 | Lessard | 15/244.2 |

FOREIGN PATENT DOCUMENTS

| | | | |
|---|---|---|---|
| 0723815 | 4/1932 | France | 15/244.1 |
| 2019220 | 10/1979 | United Kingdom | 601/137 |

*Primary Examiner*—David Scherbel
*Assistant Examiner*—James F. Hook
*Attorney, Agent, or Firm*—John R. Flanagan

[57] ABSTRACT

An applicator device for moving a contact surface against a person's back includes an elongated handle and a generally disc-shaped shell formed on one end of the handle. A generally disc-shaped cap is threadably engaged with the shell. The cap can be formed with structure for brushing, massaging, or scratching a person's back, or the cap can detachably hold one of a plurality of contact pads, with each contact pad having a structure and function distinct from the other pads.

20 Claims, 4 Drawing Sheets

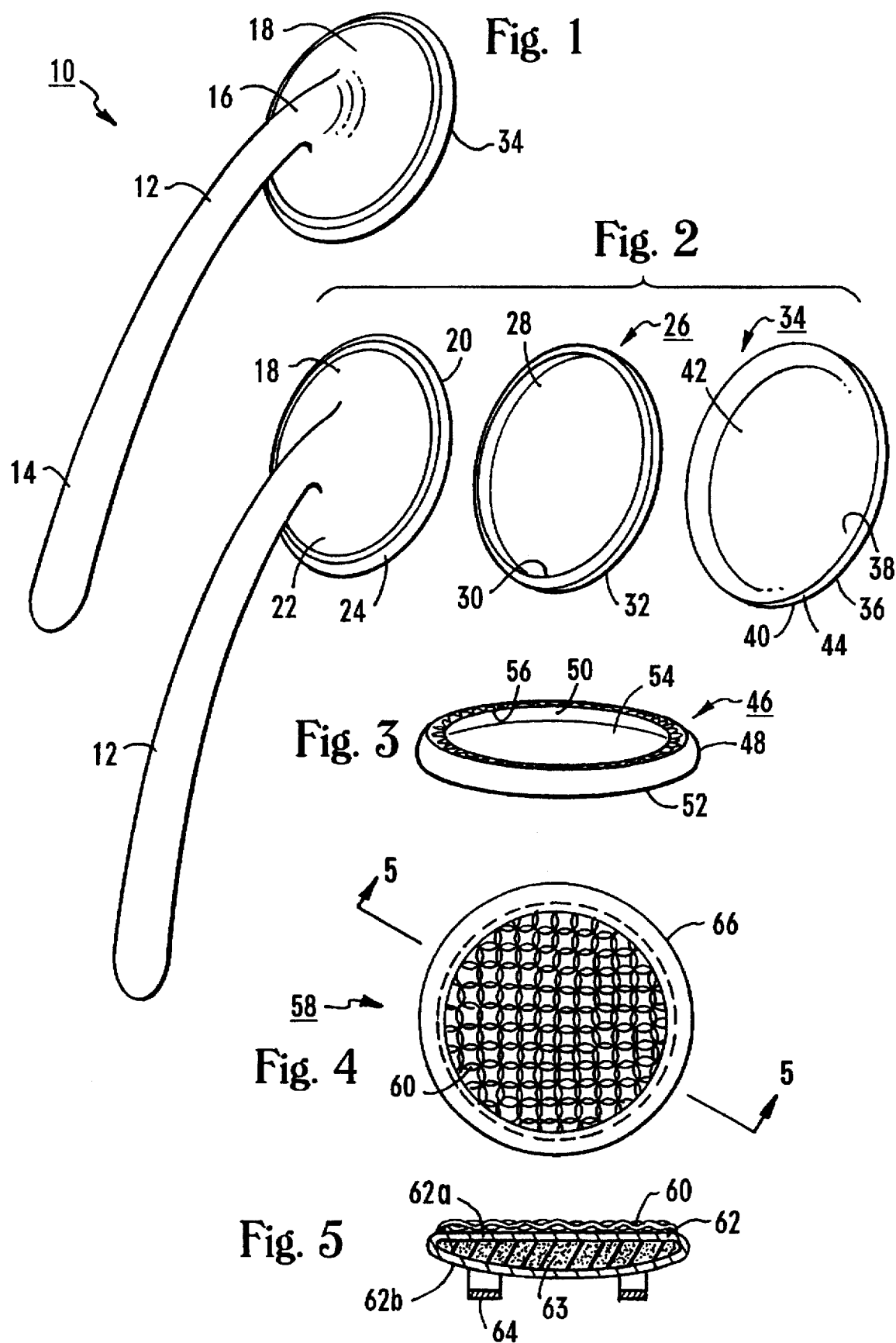

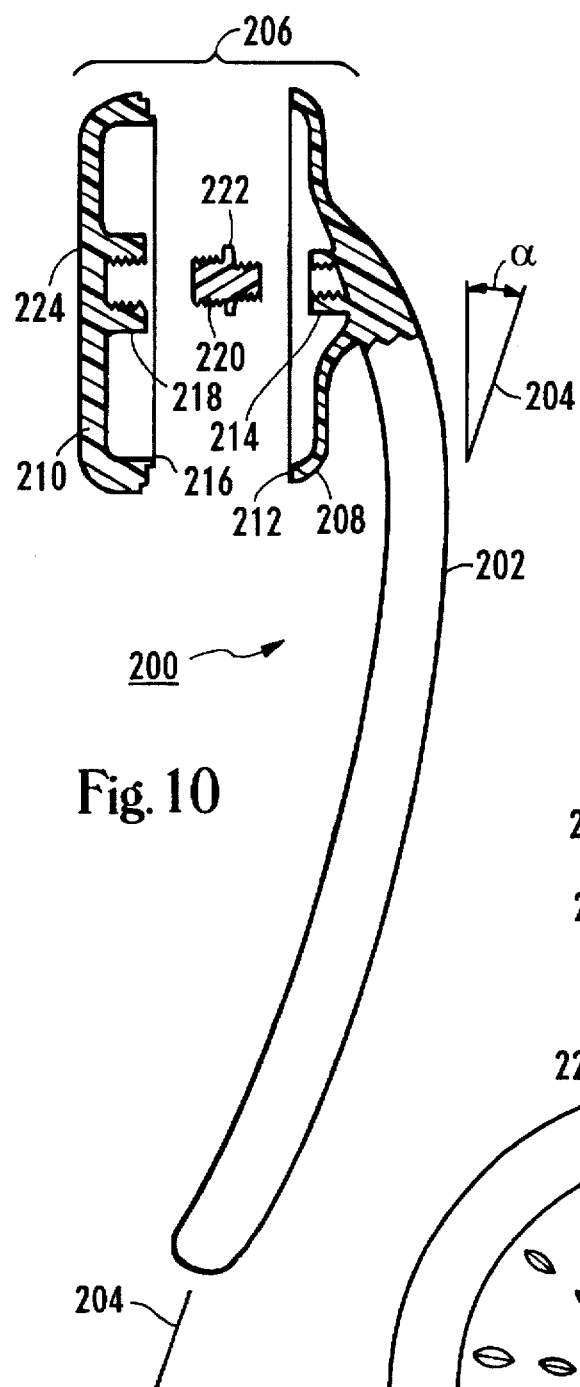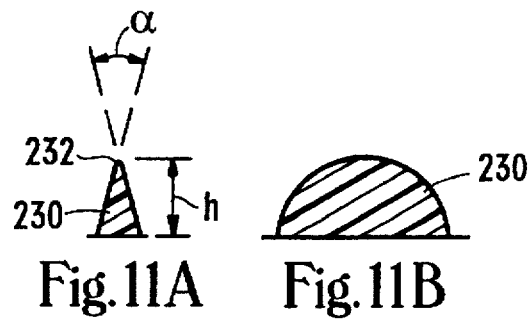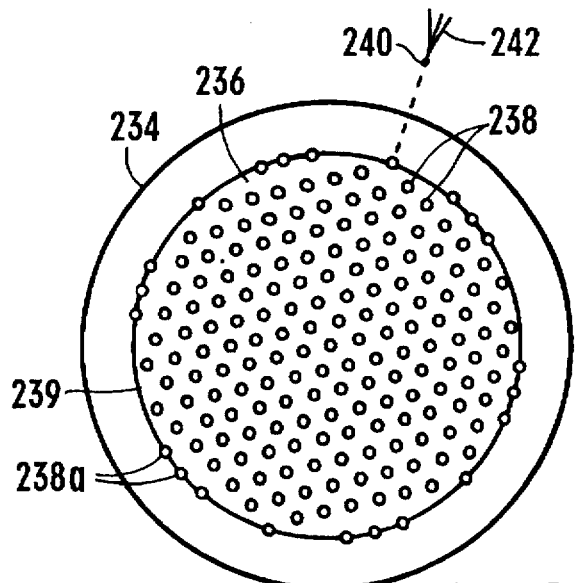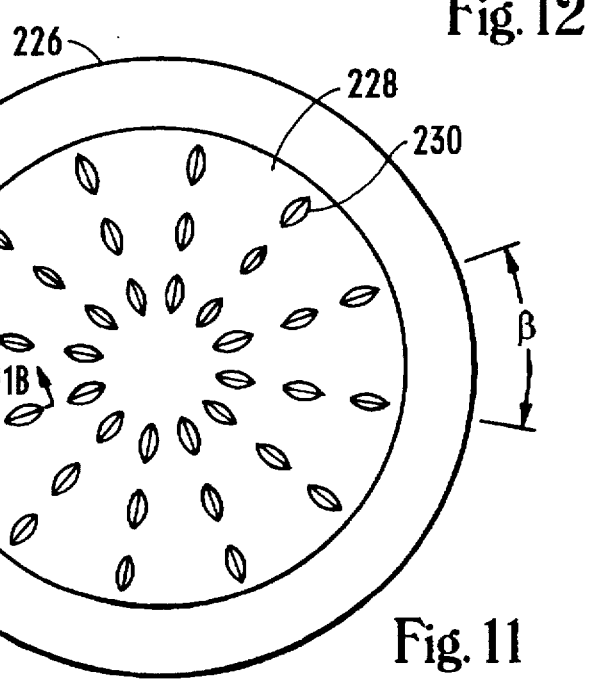
Fig. 10
Fig. 11A  Fig. 11B
Fig. 12
Fig. 11

APPLICATOR DEVICE WITH SCREW-ON ATTACHMENTS

This application is a continuation-in-part of and claims priority from pending U.S. patent application Ser. No. 08/308,642 for an invention entitled "APPLICATOR DEVICE", filed Sep. 19, 1994 in the name of Myra Per-Lee and issued Aug. 1, 1995 and U.S. Pat. No. 5,437,372, which is a continuation of U.S. patent application Ser. No. 08/107,510 for an invention entitled "APPLICATOR DEVICE", filed Aug. 17, 1993 in the name of Myra Per-Lee and issued Feb. 14, 1995 as U.S. Pat. No. 5,388,700.

FIELD OF THE INVENTION

The present invention relates generally to skin care products, and more particularly to devices for applying skin treatment substances to the back of a person.

BACKGROUND

Medical science continues to discover increasing evidence of the importance of proper skin care. For example, it has become clear that sunlight can damage a person's skin if the person's skin is repeatedly exposed to sunlight, i.e., if the person habitually remains outdoors without protective covering, e.g., clothing or suntan lotion. Such damage can include premature wrinkling and aging of the skin, and in some cases can lead to skin cancer.

While proper skin care can have remedial effects in alleviating or preventing skin damage, it can also have salubrious effects in restoring damaged skin and maintaining healthy skin. Not surprisingly, it may be desirable or necessary for a person to use a variety of skin treatment substances, depending on the particular need of the person and purpose of the skin treatment.

Accordingly, a large number of skin treatment substances are currently on the market. These substances include suntan lotions and oils, skin cleansers, skin conditioners, and so on. Typically, a person applies the desired skin treatment substance by hand, i.e., by rubbing the skin treatment substance into his or her skin.

Unfortunately, it can be difficult for a person to apply skin treatment substances to his or her own back, because it is anatomically difficult for most people to reach by hand large areas of their backs. Nevertheless, proper skin care of the back is important. Accordingly, it is not unusual for a person to receive assistance in applying skin care substances to his or her back, but such assistance is not always available or desired.

Accordingly, it is an object of the present invention to provide a device for enabling a person to personally apply skin treatments to his or her back. Another object of the present invention is to provide a device for enabling a person to apply a variety of skin care products to his or her back. Still another object of the present invention is to provide a device for proper skin care of the back which is easy to use and cost effective to manufacture.

SUMMARY OF THE INVENTION

An applicator device is disclosed for enabling a person to apply a skin treatment substance to hard-to-reach areas of the person's back. The device of the present invention includes an elongated shaft which has a first end and a second end, and the shaft includes a manually grippable segment formed adjacent the first end of the shaft. An applicator head having an applicator surface is formed on the second end of the shaft.

To cover the applicator surface of the head, a contact pad is removably engaged with the head. The contact pad can be manually removed from the head without damaging the head or pad and replaced with another contact pad.

Preferably, a resilient head pad is attached to the head for covering the applicator surface of the head. In the presently preferred embodiment, the contact pad has a flat cover portion which defines an inside surface, and the inside surface of the pad abuts the head pad. Also, the contact pad has a contact surface that is opposed to the inside surface of the pad for contacting the skin of the person.

As intended by the present invention, the contact pad has an opening and the opening has an elastic periphery. Consequently, the contact pad has an enlarged configuration, wherein the head can be moved through the opening to engage and disengage the contact pad from the head, and a gripping configuration, wherein the head cannot be moved through the opening, to thereby hold the contact pad onto the head. Preferably, the contact pad is materially biased to the gripping configuration.

Alternatively, the periphery of the opening of the contact pad is inelastic, and the pad has a flap which selectively covers the opening. The periphery can be held in the gripping configuration by fastening the flap over the opening using at least one fastener, e.g., a Velcro® fastener.

To facilitate applying a variety of skin treatment substances to the back, a plurality of contact pads is preferably provided, with each pad being individually engageable with the head. Thus, a first contact pad has a non-porous contact surface for applying relatively viscous substances, e.g., suntan lotion or cream, to the back of a person. Also, a second contact pad has a porous contact surface for retaining relatively non-viscous substances, e.g., oil or alcohol, for applying the relatively non-viscous substances to the back of a person.

Yet a third contact pad has a Velcro® contact surface for gently scratching the back of a person, and a fourth contact pad has a sisal contact surface for cleansing the back of a person.

In another aspect of the present invention, a device is manually grippable by a person to enable the person to apply a skin treatment substance to the person's back by touching the device to the person's back. The device includes a manually grippable elongated shaft and an enlarged head formed on the shaft. A contact pad is also provided, and the contact pad has a contact surface for holding the skin treatment substance. In accordance with the present invention, the contact pad has an enlarged configuration, wherein the pad can be manually engaged and disengaged with the head without damaging the pad or head, and a gripping configuration, wherein the pad is held onto the head. When the contact pad is in the gripping configuration, the person can manipulate the shaft to cause the contact pad to contact the person's back and thereby apply the skin treatment substance to the person's back. Advantageously, a bag can be provided for holding and carrying the shaft and the contact pads.

In yet another aspect of the present invention, an applicator kit is disclosed for applying a selectable one of a plurality of skin treatment substances to the skin of a person. The kit of the present invention includes a shaft having a head formed thereon. A first contact pad is engageable with the head, and the first pad has a non-porous contact surface for applying relatively viscous skin treatment substances to the skin of the person. Also, the kit includes a second contact pad engageable with the head, wherein the second pad has a porous contact surface for retaining relatively non-viscous skin treatment substances for applying the relatively non-viscous skin treatment substances to the skin of the person. Further, the kit includes a third contact pad engageable with the head, wherein the third pad has a sisal contact surface for cleansing the skin of the person. Additionally, the kit includes a bag having a first cavity for holding the shaft and a second cavity for holding the contact pads. One contact pad at a time can be selectively engaged and disengaged with the head without damaging the contact pad or the head.

In still another aspect of the present invention, an applicator device has an elongated shaft having a first end and a second end, and the shaft includes a manually grippable segment formed adjacent the first end of the shaft. An applicator head is formed on the second end of the shaft, and the head has an applicator surface. A contact pad is removably engaged with the head for covering the applicator surface. The pad has a contact surface made of a plastic abrasive material, such as Velcro®, and the contact pad can be manually removed from the head without damaging the head or pad and replaced with another contact pad.

In an alternate embodiment, an applicator device includes an elongated curved shaft that has a first end and a second end. The shaft includes a manually grippable segment formed adjacent the first end of the shaft. An applicator head is formed on the second end of the shaft, and a contact pad is engageable with the head.

As intended by the present invention, the contact pad is selected from the group of pads consisting of a hollow sponge pad that has a continuous sponge contact surface and an opposed engagement surface formed with a slit. A chamber is established between the surfaces for receiving the head, and the head can pass through the slit into the chamber to hold the sponge pad on the head.

The group of pads also includes a knitted single piece exfoliator pad which has a polypropylene contact surface and a periphery for receiving the head therethrough to hold the exfoliator pad onto the head. Also, the group of pads includes an exfoliator pad with nylon or polypropylene net attached to an elastic sleeve that is positionable over the head to hold the exfoliator pad onto the head. Furthermore, the group of pads includes a loofah attachment pad including a skirt that is positionable over the head to hold the loofah attachment pad onto the head.

In one preferred embodiment, the engagement surface of the sponge pad is biased toward a closed configuration, wherein the slit is closed. The engagement surface can be moved to an open configuration, wherein the head can pass through the slit.

Preferably, the skirt of the loofah attachment pad forms a periphery and the periphery is circumscribed by a drawstring. The drawstring can be manipulated to reduce the periphery to prevent the head from passing through the periphery.

In another aspect of the present invention, an applicator device includes an elongated, gently curved handle and a head attached to one end of the handle. In accordance with the present invention, the head includes an enlarged shell and a complementarily-shaped cap which is detachably engaged with the shell. A contact surface is associated with the head for contacting the skin of a person.

Preferably, the cap is threadably engaged with the shell, and the contact surface is formed integrally with the cap. In one embodiment, the contact surface includes a plurality of projections for gently scratching a person's back. On the other hand, in another embodiment, the contact surface includes a plurality of holes, and the device further comprises a plurality of bristle tufts, with each tuft being anchored in a respective hole. Or, the contact surface may include structure for massaging a person's back. As intended by the preferred embodiment, this structure includes a plurality of gently contoured, preferably cylindrical protrusions, and the protrusions may be formed integrally with the contact surface or rotatably mounted with respect to the contact surface.

To permit the cap to be detachably engaged with the shell, the shell defines a periphery and is formed with a threaded shell fitting that is centrally located relative to the periphery of the shell and is distanced therefrom. Likewise, the cap defines a periphery and is formed with a threaded cap fitting centrally located relative to the periphery of the cap and distanced therefrom. As envisioned by the present invention, the cap fitting is formed complementarily to the shell fitting for engaging the shell fitting.

In still another aspect of the alternate embodiment, an applicator device for moving a contact surface against a person's back includes an elongated handle and a generally disc-shaped shell formed on one end of the handle. A generally disc-shaped cap is detachably engaged with the shell and is operably associated with the contact surface.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a perspective view of the applicator device of the present invention;

FIG. 2 is an exploded perspective view of the applicator device;

FIG. 3 is a perspective view of the oils and liniment applicator;

FIG. 4 is a top view of the cleansing applicator;

FIG. 5 is a cross-sectional view as would be seen along the line 5—5 in FIG. 4;

FIG. 10 is an exploded partial cross-sectional side view of an alternate embodiment of the present invention, showing a handle with head and threadably engageable cap;

FIG. 11 is a perspective view of a scratcher cap for engaging the handle shown in FIG. 10;

FIG. 11A is a transverse cross-sectional view of one of the scratcher elements, as seen along the line 11A—11A in FIG. 11;

FIG. 11B is a longitudinal cross-sectional view of one of the scratcher elements, as seen along the line 11B—11B in FIG. 11;

FIG. 12 is a plan view of a brush attachment cap for engaging the handle shown in FIG. 10, with on tuft of bristles shown in an exploded relationship and the remainder of the bristles removed for clarity;

DETAILED DESCRIPTION OF THE PREFERRED EMBODIMENT

Figure 6:
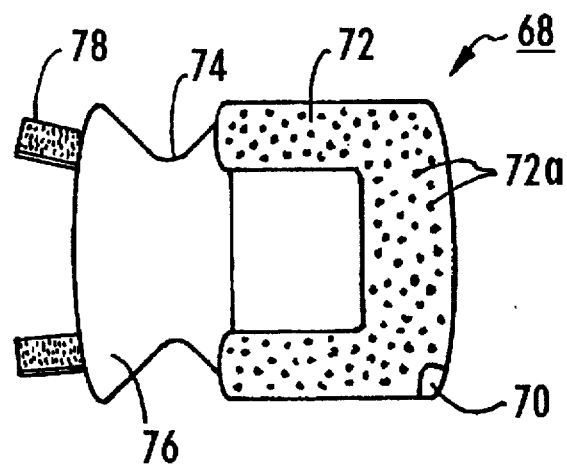
FIG. 6 is a perspective view of the back scratcher, with the flap in the open position.

Referring initially to FIG. 1, an applicator device for applying skin treatment substances to a person's back is shown, generally designated 10. As shown, the device 10 includes an elongated manually grippable hollow shaft 12 having a handle segment 14 and a head end 16. The shaft 12 is gently curved along its dimension of elongation.

In cross-reference to FIGS. 1 and 2, a generally disc-shaped head 18 is formed on the head end 16 integrally with the shaft 12. The head 18 has a flat or slightly convex applicator surface 20, a rear surface 22 opposed to the applicator surface 20, and a periphery 24 established therebetween. As shown, the plane established by the applicator surface 20 is generally parallel to the longitudinal dimension of the shaft 12. Consequently, the applicator surface 20 can be positioned against the back of a person when the person grips the handle segment 14 and manipulates it appropriately.

Preferably, the shaft 12 and head 18 are made of a unitary piece of injection molded acrylic or cellulose acetate. Alternatively, the shaft 12/head 18 can be blow molded polyethylene. Other materials, however, e.g., polyurethane, polypropylene, acrylic, other plastics, and wood, can also be used.

FIG. 2 best shows that a resilient head pad, generally designated 26, is positioned against the applicator surface 20 of the head 18 to cover the applicator surface 20. The head pad 26 is configured to conform to the head 18 and to tightly grip the head 18.

More specifically, the head pad 26 has an opening 28 defining an elastic periphery 30. It will be appreciated in reference to FIG. 2 that the periphery 30 of the resilient head pad 26 can be deformed slightly to permit positioning the applicator surface 20 of the head 18 through the opening 28 of the head pad 26 to abut a pad surface 32 of the head pad 26. As shown in FIG. 2, the pad surface 32 of the head pad 26 is shaped like the applicator surface 20 of the head 18.

Once the head pad 26 is positioned onto the head 18, the periphery 30 of the head pad 26 grips the rear surface 22 of the head 18 to tightly hold the head pad 26 onto the head 18.

Preferably, the head pad 26 is made of silicon having a durometer rating of twenty-five to forty-five (25–45) shore, and preferably thirty to forty (30–40) shore. Consequently, the head pad 26 can cushion the head 18, is durable and wear-resistant, and will not readily absorb skin treatment substances. Alternatively, the head pad 26 can be made of latex.

Still referring to FIG. 2, a non-porous, stretchable, preferably thin powdered latex lotion and cream contact pad, generally designated 34, is configured to conform to the head pad 26 and is removably attached to the head pad 26. As shown in FIG. 2, the lotion and cream contact pad 34 has a flat cover portion 36 which is configured like the pad surface 32 of the head pad 26, and the cover portion 36 defines an inside surface 38 which abuts the head pad 26. A contact surface 40 is opposed to the inside surface 38 for contacting the skin of a person.

Additionally, the lotion and cream contact pad 34 has an opening 42, and the opening 42 defines an elastic periphery 44 which is established by a roll of latex material formed integrally with the cover portion 36. Consequently, the lotion and cream contact pad 34 has an enlarged configuration, wherein the head pad 26 can be moved through the opening 42 to engage and disengage the lotion and cream contact pad 34 from the head pad 26, and a gripping configuration, wherein the periphery 44 of the pad 34 grips the head pad 26. With the contact pad 34 positioned on the head pad 26 in the gripping configuration, the head pad 26 is disposed within the opening 42. The lotion and cream contact pad 34 is thereby held onto the head 18. From the disclosure above, it is to be appreciated that the lotion and cream contact pad 34 is materially biased into the gripping configuration.

The skilled artisan will appreciate that by making the lotion and cream contact pad 34 from latex, the pad 34 imitates the feel of human skin, and will not readily absorb relatively viscous substances, e.g., suntan lotion and cream. The contact surface 40 of the lotion and cream contact pad 34 will, however, hold relatively viscous substances for applying such substances to human skin when the contact surface 40 is rubbed against the skin.

Also, latex is relatively inexpensive, so that the lotion and cream contact pad 34 can be a single use, disposable item for promoting hygiene. Thus, after use of the pad 34, the pad 34 manually can be moved to the enlarged configuration, manually removed from the head pad 26, and replaced by another like pad (not shown) for use of the applicator device 10 by another or the same person, without damaging either the pad 34 or head 18.

Now referring to FIG. 3, a single-use, disposable oil and liniment contact pad is shown, generally designated 46. It is to be understood that the oil and liniment contact pad 46 can be held onto the head pad 26 in place of the lotion and cream contact pad 34 to apply relatively non-viscous substances, e.g., body oil, alcohol, and liniment, to the skin of a person.

Accordingly, the oil and liniment contact pad 46 is made of a porous material, to enable the pad 46 to hold non-viscous substances. In one presently preferred embodiment, the oil and liniment contact pad 46 is made of a polypropylene cloth, e.g., the cloth material made by Kimberly-Clark Corp. and marketed under the trade designation "CREW WIPER 33330". Alternatively, the oil and liniment contact pad 46 can be made of another porous material, e.g., cotton cloth or cloth made of other suitable fabric.

As shown in FIG. 3, the oil and liniment contact pad 46 has a flat cover portion 48 which is configured like the pad surface 32 of the head pad 26, and the cover portion 48 defines an inside surface 50 which abuts the head pad 26. A contact surface 52 is opposed to the inside surface 50 for contacting the skin of a person.

Additionally, the oil and liniment contact pad 46 has an opening 54, and the opening 54 defines an elastic periphery 56. The periphery 56 of the opening 54 is established by a continuous elastic strip (not shown in FIG. 3), and the cover portion 48 is sewn to the elastic strip in a bunched configuration as is well-known in the art. Consequently, the oil and liniment contact pad 46 has an enlarged configuration, wherein the head pad 26 can be moved through the opening 54 to engage and disengage the oil and liniment contact pad 46 from the head pad 26, and a gripping configuration, wherein the periphery 56 of the pad 46 grips the head pad 26. With the contact pad 46 positioned on the head pad 26 in the gripping configuration, the head pad 26 cannot be moved through the opening 54. The oil and liniment contact pad 46 is thereby held onto the head 18. From the disclosure above, it is to be appreciated that the oil and liniment contact pad 46 is materially biased into the gripping configuration.

FIGS. 4 and 5 show a cleansing pad, generally designated 58, which can be attached to the head pad 26 in lieu of the pads 34, 46 disclosed above to cleanse and defoliate the skin of a person's back. As shown, the cleansing pad 58 has a scrubbing surface 60 which is made of a material that can scrub the skin of a person's back. In the presently preferred embodiment, the scrubbing surface 60 is made of knitted sisal.

As can best be appreciated in reference to FIG. 5, the scrubbing surface 60 is sewn to a terry cloth back 62. Preferably, the back includes a top layer 62a and a bottom layer 62b, and a sponge layer 63 is sandwiched between the layers 62a, 62b. The layers 62a, 62b of the terry cloth back 62 can be made from a unitary piece of cloth, or from separate pieces of cloth which are sewn together. Together, the terry cloth back 62 and sponge layer 63 can hold a cleansing substance, e.g., soapy water.

The cleansing pad 58 also includes a plurality of elastic straps 64, each of has two opposed ends attached to a periphery 66 of the back surface 62. Each strap 64 is distanced from the back surface 62 between the respective ends of the strap 64. Consequently, the elastic straps 64 can be manually deformed, and the head 18 with head pad 26 advanced between the elastic straps 64 and the back surface 62 of the cleansing pad 58. Then, the straps 64 are permitted to return to the biased configuration shown in FIG. 5 to hold the cleansing pad 58 onto the head pad 26. It is to be understood that the straps 64 can be omitted, and the periphery 66 elasticized in accordance with the principles discussed above regarding the oil and liniment contact pad 46, to hold the cleansing pad 58 onto the head pad 26.

FIG. 6 shows a back scratcher, generally designated 68, which can be attached to the head pad 26 in lieu of the pads 34, 46, 58 disclosed above to gently scratch the back of a person. As show, the back scratcher 68 has a contact surface 70 and a fastening surface 72 which is formed integrally with the contact surface 70 and folded back from the contact surface 70. Notches 74 are formed in the contact surface 70 to permit easily folding the fastening surface 72 back from the contact surface 70.

In the presently preferred embodiment, the contact surface 70 and fastening surface 72 are made of a plastic abrasive material, preferably Velcro® hook type 88 material, for gently scratching human skin without unduly abrading the skin. As is known in the art, Velcro® hook material consists of a plurality of tightly bunched, small plastic bristle-like hooks 72a. A flap 76 is formed integrally with the contact surface 70, and a plurality of fasteners 78 are attached to the flap 76. Each fastener is made of Velcro® loop type 1000 material for engaging the Velcro® hook material of the fastening surface 72.

Accordingly, the back scratcher 68 has an open configuration (shown in FIG. 6), wherein the fasteners 78 are distanced from the fastening surface 72 to permit positioning the head 18 with head pad 26 between the back surface 72 and the contact surface 70. Also, the back scratcher 68 has a closed configuration (not shown), wherein the fasteners 78 are attached to the fastening surface 72 to hold the back scratcher 68 onto the head 18 with head pad 26.

From the disclosure above, it is to be appreciated that any one of the pads 34, 46, 58, 68 can be manually individually engaged and disengaged with the head 18 without damaging the pads 34, 46, 58, 68 or head 18. Further, it is to be appreciated that because of the material of which it is made, the silicon head pad 26 has a high coefficient of friction, and the pads 34, 46, 58, 68 cannot consequently slide relative to the head pad 26 when the particular pad 34, 46, 58, 68 that is engaged with the head pad 26 is rubbed against human skin.

Figure 7:
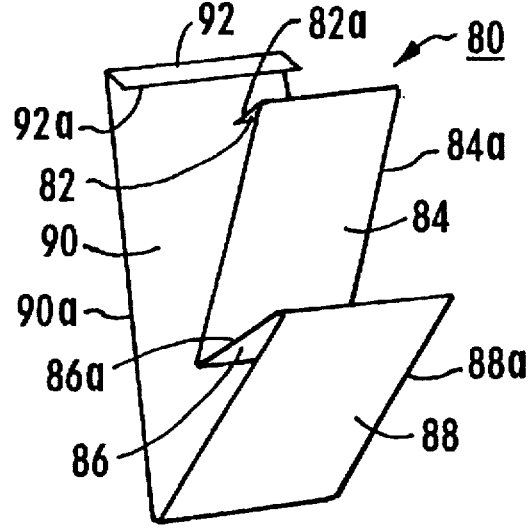
FIG. 7 is a perspective view of the carrying bag of the present invention during manufacture.
Figure 8:
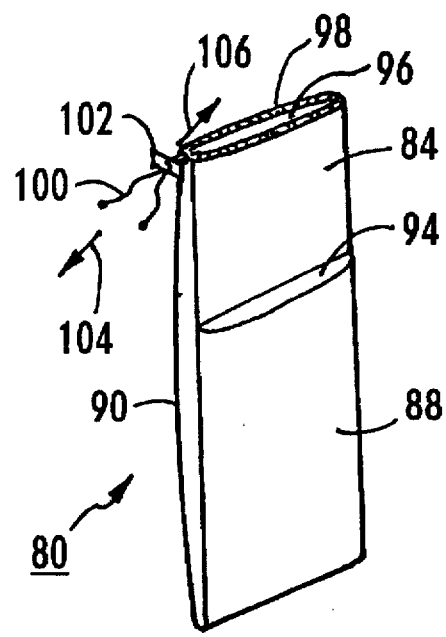
FIG. 8 is a perspective view of the carrying bag of the present invention.

FIGS. 7 and 8 show that carrying bag, generally designated 80, can be provided for holding and transporting the shaft 12 and pads 34, 46, 58, 68 disclosed above. As can be appreciated in reference to FIG. 7, the bag 80 is preferably made from a single bolt of material. In the presently preferred embodiment, the bag 80 is made from a machine washable, water repellant, and protective material, e.g., the material marketed by Fabri-Quilt of North Kansas City, Mo., under the designation type 128 downproof rip-stop nylon material.

In cross-reference to FIGS. 7 and 8, the bag 80 has first through sixth panels 82, 84, 86, 88, 90, 92, and each panel 82, 84, 86, 88, 90, 92 has a respective edge 82a, 84a, 86a, 88a, 90a, 92a. The panels are folded relative to each other, as shown, and the edge 86a of the third panel 86 is sewn to the edge 84a of the second panel 84 to establish a first cavity 94. Also, the edges 84a, 88a of the second and fourth panels 84, 88 are sewn to the edge 90a of the fifth panel 90 to establish a second cavity 96. Further, the edges 82a, 92a of the first and sixth panels 82, 92 are respectively sewn to the second and fifth panels 84, 90 to establish a hollow peripheral border 98 of the second cavity 96. As shown in FIG. 7, the hollow peripheral border 98 has an open configuration, wherein the shaft 12 with head 18 can be advanced into the second cavity 96.

A drawstring 100 can be positioned within the hollow border 98, and the drawstring 100 is also operably engaged with a pull tab 102. Accordingly, the drawstring 100 can be pulled in the direction indicated by the arrow 104, and the pull tab 102 can be pulled in the direction indicated by the arrow 106, to move the border 98 to a closed configuration for enclosing the shaft 12 within the second cavity 96. On the other hand, the pads 34, 46, 58, 68 can be carried in the first cavity 94.

Figure 9:
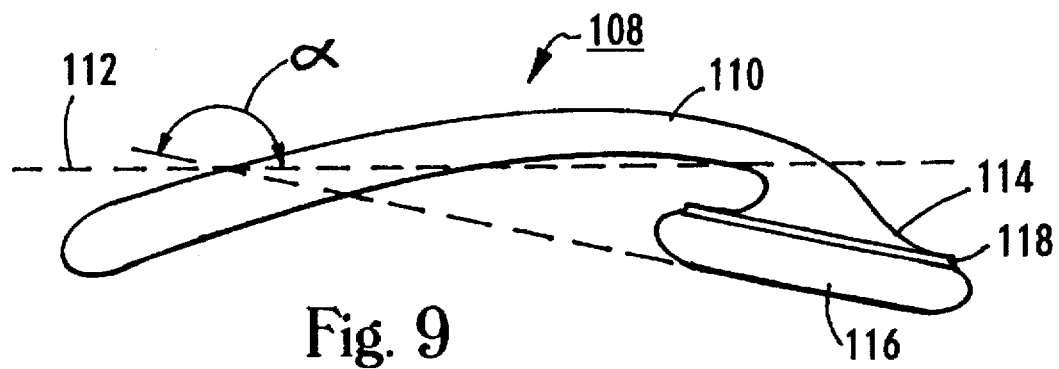
FIG. 9 is a side view of an alternate embodiment of the applicator device of the present invention.

FIG. 9 shows that in an alternate embodiment, an applicator device 108 has an elongated shaft 110 roughly defining a longitudinal axis 112, and the device 108 further includes a disc-shaped head 114 having an applicator surface 116. The plane defined by the surface 116 establishes an oblique angle α of less than 180 degrees with respect to the axis 112. Stated differently, the surface 116 is inclined with respect to the axis 112 of the shaft 110. With this arrangement, a person is permitted to more easily position the surface 116 flush against the person's back when the person grips the shaft 110. If desired, a groove 118 can be formed on the head 114 to provide a seating surface for the periphery 44 of the contact pad 34 shown in FIGS. 1 and 2.

FIG. 10 shows that in yet another alternate embodiment, an applicator device 200 has an elongated shaft 202 roughly defining a longitudinal axis 204, and the device 200 further includes a generally disc-shaped head 206. In contrast to the unitarily-formed heads shown in the previously described embodiments, however, the head 206 shown in FIG. 10 is a multi-piece component. More specifically, the head 206 includes a hollow, generally disc-shaped shell 208 which is enlarged relative to the shaft 202, and a hollow, generally disc-shaped cap 210 is detachably engaged with the shell 208 to establish the head 206.

In the preferred embodiment, the cap 210 is threadably engaged with the shell 208. It is to be understood, however, that the cap 210 can be snappingly engaged with the shell 208 or engaged with the shell 208 in an interference fit.

As shown in FIG. 10, the shell 208 defines a periphery 212, and a hollow cylindrical internally threaded shell fitting 214 is formed on the shell 208. More particularly, the shell fitting 214 is centrally located relative to the periphery 212 of the shell 208 and is distanced from the periphery 212 of the shell 208.

Additionally, the cap 210 defines a periphery 216, and a hollow cylindrical internally threaded cap fitting 218 is formed on the cap 210. More particularly, the cap fitting 218 is centrally located relative to the periphery 216 of the cap 210 and is distanced from the periphery 216 of the cap 210.

Furthermore, a cylindrical externally threaded male adapter 220 having a central disc-shaped collar 222 is threadably engaged with the shell fitting 214. It will be appreciated that when the shell fitting 214 includes the male adapter 220, the shell fitting 214 is a male fitting. If desired, the male adapter 220 can be bonded to the shell fitting 214 by, e.g., solvent bonding or mechanical torqueing, or the male adapter 220 can be formed integrally with the shell 208.

As the skilled artisan will further appreciate, the cap fitting 218 is formed complementarily to the shell fitting 214 with male adapter 220. Consequently, the cap fitting 218 can threadably engage the shell fitting 214 with male adapter 220 to detachably engage the cap 210 with the shell 208.

Still referring to FIG. 10, the cap 210 is formed with a flat disc-shaped applicator surface 224. When the cap 210 is engaged with the shell 208, the plane defined by the applicator surface 224 establishes an oblique angle $\alpha'$ of between about twenty (20) degrees and thirty (30) degrees, to facilitate the positioning, by a person having a limited range of motion, of the applicator surface 224 against the person's back.

It is to be understood that any one of the applicator contact pads disclosed below, or any one of the previously-disclosed pads, can be removably engaged with the head 206 of the device 200 shown in FIG. 10. In the preferred embodiment shown, the applicator surface 224 is smooth. If desired, however, the surface 224 can be slightly roughened to meet mold tech finish standard #MT-11040 to reduce slippage of the pad on the applicator surface 224 when the pad is rubbed against a person's back.

In cross-reference to FIGS. 10 and 11, the cap 210 can be disengaged from the shell 208 and replaced with a scratcher cap 226. As shown in FIG. 11, the scratcher cap 226 is formed with a contact surface 228, and a plurality of outwardly-oriented projections 230 are formed on the contact surface 228 for gently scratching a person's skin when the scratcher pad 226 is moved against the skin. It is to be understood that the scratcher cap 226 includes a fitting like the cap fitting 218 shown in FIG. 10, for permitting threadably engaging the scratcher cap 226 with the shell 208.

FIG. 11 shows that in the presently preferred embodiment, the projections 230 are arranged in a twelve rows of three projections each, with each row being separated from its immediately adjacent row by an angle $\beta$ of about thirty (30) degrees. As intended by the present invention, each projection 230 is shaped somewhat like a half discus.

Specifically, each projection 230 is thin, growing slightly thicker from the top (i.e., most outwardly-oriented) part 232 of the projection 230 (best shown in FIG. 11A) toward the plane defined by the surface 228. Also, each projection 230 is somewhat elongated, with the longitudinal axis of each projection 230 being oriented along a radial of the scratch cap 226 as shown. Consequently, at least some of the projections 230 will present a broad aspect to the skin for effective scratching of the skin, regardless of the direction in which the scratch cap 226 is moved across the skin.

FIGS. 11A and 11B best illustrate the configuration of each projection 230. As shown in FIG. 11A, each projection 230 in transverse cross-section is generally wedge-shaped, with the sides of each projection 230 defining an angle $\gamma$ of about thirty five (35) degrees. The height "h" of each projection 230 is preferably about one-eighth inch (0.125"). Further, the top part 232 of each projection 230 is not pointed, but is tightly rounded, with a radius of curvature of about fifteen thousandths of an inch (0.015"). FIG. 11b shows that in contrast, in longitudinal cross-section each projection 230 is semicircularly-shaped.

FIG. 12 shows that a brush cap 234 can be engaged with the shell 208 by means previously described. As shown, the brush cap 234 includes a contact surface 236 formed with a plurality of one-tenth inch (0.10041) diameter holes 238. A tuft 240 of bristles 242 is anchored in each hole 238 by means well-known in the brush art, e.g., by staple anchoring or by anchor bar anchoring. Each bristle 242 is made of appropriate bristle material, e.g., boar's hair, nylon, or other suitable natural or synthetic material. As shown, a plurality of edge holes 238a can be formed along the periphery 239 of the contact surface 236.

Figure 13:
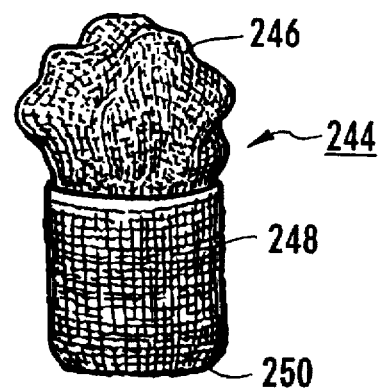
FIG. 13 is a perspective view of a nylon net exfoliator pad.

FIGS. 13–16 show additional applicator pads which can be selectively engaged with any one of the applicator devices shown in FIGS. 1, 9, and 10. Referring first to FIG. 13, a nylon net exfoliator pad 244 includes a balled nylon net 246 sewn to a hollow, generally cylindrical elastic sleeve 248. The elastic sleeve 248 defines a periphery 250, and the elastic sleeve 248 is positionable over one of the applicator heads shown above by deforming (i.e., stretching) the sleeve 248 to permit passing the head through the periphery 250. Then, the sleeve 248 is released to contract and thereby hold the nylon net exfoliator pad 244 onto the head.

Figure 14:
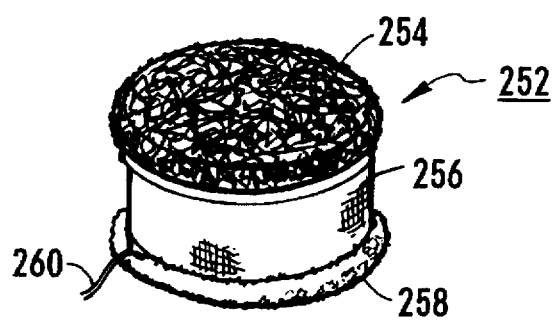
FIG. 14 is a perspective view of a loofah pad.

FIG. 14 shows a hollow cylindrical loofah attachment pad 252 having a sponge-backed loofah contact surface 254 and a cloth skirt 256. The cloth skirt 256 defines a periphery 258, and the periphery 258 is circumscribed by a drawstring 260. It will be appreciated that the skirt 256 is positionable over one of the applicator heads shown above to hold the loofah attachment pad 252 onto the head. More particularly, after the skirt 256 has been fitted over the head, the drawstring 260 can be manipulated to reduce the periphery 258 of the skirt 256 to prevent the head from passing through the periphery 258.

Figure 15:
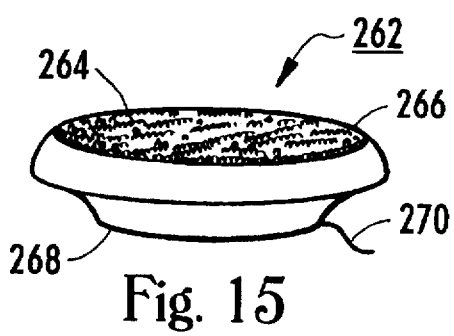
FIG. 15 is a perspective view of a knitted single piece polypropylene exfoliator pad.

FIG. 15 shows a knitted single piece exfoliator pad 262 having a contact surface 264 that includes polypropylene loops 266. As shown, the exfoliator pad 262 defines a periphery 268 for receiving one of the heads disclosed above therethrough. Also, a drawstring 270 circumscribes the periphery 268 and can be manipulated to hold the single piece exfoliator pad 262 onto the head.

Figure 16:
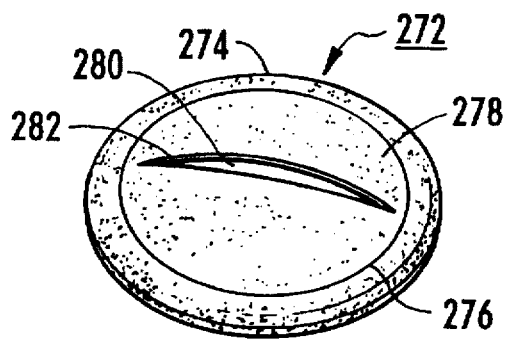
FIG. 16 is a perspective view of a slitted hollow sponge pad.

Now referring to FIG. 16, a hollow sponge pad 272 includes a top sponge half 274 that defines a continuous sponge contact surface. Opposed to the top sponge half 274 and sewn to it is a bottom sponge half 276 which defines an engagement surface 278. A chamber 280 is established between the sponge halves 274, 276.

As shown in FIG. 16, the engagement surface 278 is formed with a slit 282. As the skilled artisan will appreciate, any one of the heads shown above can pass through the slit 282 into the chamber 280 to hold the sponge pad 272 onto the head. Stated differently, the engagement surface 278 of the sponge pad 272 is biased toward a closed configuration, wherein the slit 282 is closed, and the engagement surface 278 can be manually moved to an open configuration, wherein the head can pass through the slit 282.

Figure 17:
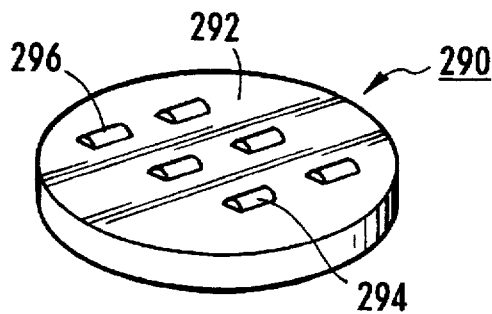
FIG. 17 is a perspective view of a massager cap for engaging the handle shown in FIG. 10.

Now referring to FIG. 17, a massager cap is shown, generally designated 290. It is to be understood that the massager cap 290 includes a fitting like the cap fitting 218 shown in FIG. 10, for permitting threadably engaging the massager cap 290 with the shell 208.

As shown, the massager cap 290 includes an applicator surface 292, and a plurality of protrusions 294 are formed integrally on the surface 292 and project outwardly therefrom for massaging a person's skin when the protrusions 294 are moved against the skin. To this end, each protrusion 294 is formed with a gently contoured contact surface 296. In the preferred embodiment shown, each protrusion 294 defines a half-cylinder. Consequently, the contact surfaces 296 of the protrusions 294 are rounded half-cylinders.

Figure 18:
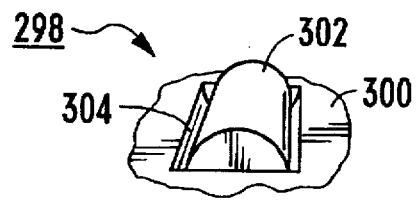
FIG. 18 is a perspective view of an alternate embodiment of the massager cap of the present invention, showing a massaging protrusion rotatably engaged with the cap, with portions of the cap broken away for clarity.
Figure 18A:
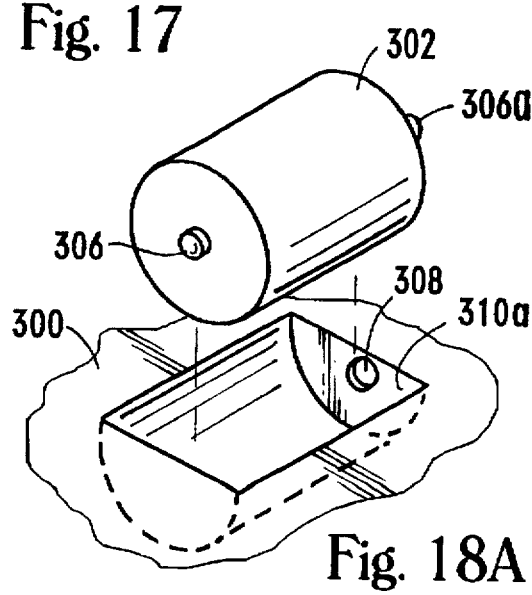
FIG. 18A is an exploded perspective view of the massager cap shown in FIG. 18.
Figure 19:
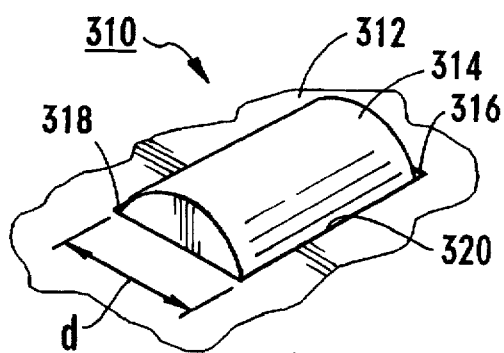
FIG. 19 is a perspective view of still another alternate embodiment of the massager cap of the present invention, showing a massaging protrusion rotatably engaged with the cap, with portions of the cap broken away for clarity.

FIGS. 18, 18A, and 19 show that alternatively, a massaging cap can be provided which includes rotatable massaging protrusions. More particularly, FIGS. 18 and 18A show a massager cap, generally designated 298, having an applicator surface 300 and a plurality of cylindrical protrusions 302 (only one protrusion 302 shown for clarity) rotatably mounted with respect thereto.

It is to be understood that in the particular embodiment shown in FIGS. 18 and 18A, a plurality of recesses 304 are formed on the cap 298, although only a single recess 304 is shown. Each recess 304 is formed complementarily to and slightly larger than a protrusion 302 for rotatably receiving a respective protrusion 302 therein. The opposed bases of each protrusion 302 are formed with respective cylindrical detents 306a, 306b, and each detent 306a, 306b rotatably engages a respective complementarily-formed cavity that is formed in opposed transverse walls of the recess 304 (only cavity 308a and transverse wall 310a shown in FIG. 18A).

FIG. 19 shows a massager cap, generally designated 310, having an applicator surface 312 and a plurality of gently contoured cylindrical protrusions 314 (only one protrusion 314 shown for clarity) rotatably mounted with respect thereto.

It is to be understood that in the particular embodiment shown in FIG. 19, a plurality of recesses 316 are formed on the cap 310, although only a single recess 316 is shown. Each recess 316 is formed complementarily to and slightly larger than a protrusion 314 for rotatably receiving a respective protrusion 314 therein.

Unlike the protrusions shown in FIGS. 18 and 18A, however, the protrusions 314 shown in FIG. 19 are not formed with engagement detents. Rather, to rotatably retain the protrusion 314 within the cavity 316, the cavity 316 is formed with an upper edge 318 and a lower edge 320, and the distance "d" between the edges 318, 320 is slightly less than the diameter of the associated protrusion 314.

Accordingly, the skilled artisan will appreciate that the protrusion 314 can be pressed between the edges 318, 320 and into the recess 316 during manufacture. The edges 318, 320 deform slightly when the protrusion 314 is pressed between them. Then, owing to the material bias of the edges 318, 320, the edges 318, 320 resume the configuration shown in FIG. 19 once the protrusion 314 has been positioned as shown within the cavity 316, thereby retaining the protrusion 314 within the cavity 316. The protrusion 314, however, is free to rotate within the cavity 316.

It is to be understood that while six (6) protrusions 294 are shown in FIG. 17, greater or fewer protrusions can be provided. Also, the relative size of the protrusions 294, 302, 314 can be different than that shown. Still further, the protrusions 294, 302, 314 can have gently contoured shapes other than cylindrical, e.g., the protrusions 294, 302, 314 can be spherical or hemispherical.

While the particular applicator device as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. An applicator device, comprising:
    an elongated curved shaft having a first end and a second end, the shaft including a manually grippable segment formed adjacent the first end of the shaft;
    an applicator head formed on the second end of the shaft, wherein the head includes an enlarged shell and complementarily-shaped cap detachably engaged with the shell, wherein the shell defines a periphery and is formed with a threaded shell fitting centrally located relative to the periphery of the shell and distanced therefrom, and the cap defines a periphery and is formed with a threaded cap fitting centrally located relative to the periphery of the cap and distanced therefrom, the cap fitting being formed complementarily to the shell fitting for engaging the shell fitting; and
    a contact pad engageable with the head, the contact pad being selected from the group of pads consisting of:
        a hollow sponge pad having a continuous sponge contact surface and an opposed engagement surface formed with a slit therein, wherein a chamber for receiving the head is established between the surfaces of the sponge pad and the head can pass through the slit into the chamber to hold the sponge pad on the head;
        a knitted single piece exfoliator pad having a polypropylene contact surface and defining a periphery for receiving the head therethrough to hold the knitted single piece exfoliator pad onto the head;
        an exfoliator pad having a nylon or polypropylene net and an elastic sleeve fixedly attached to the nylon net, wherein the elastic sleeve is positionable over the head to hold the nylon net exfoliator pad onto the head; and
        a loofah attachment pad having a sponge-backed loofah contact surface and a skirt positionable over the head to hold the loofah attachment pad onto the head.

2. The applicator device of claim 1, wherein the engagement surface of the sponge pad normally assumes a closed configuration, wherein the slit is closed, and wherein the engagement surface can be manually moved to an open configuration, wherein the head can pass through the slit.

3. The applicator device of claim 1, wherein the skirt of the loofah attachment pad forms a periphery and the periphery is circumscribed by a drawstring, and the drawstring can be manipulated to reduce the periphery to prevent the head from passing through the periphery.

4. An applicator device, comprising:

an elongated gently curved handle;

a head attached to one end of the handle, the head including an enlarged shell and a complementarily-shaped cap detachably threadably engaged with the shell, wherein the shell defines a periphery and is formed with a threaded shell fitting centrally located relative to the periphery of the shell and distanced therefrom, and the cap defines a periphery and is formed with a threaded cap fitting centrally located relative to the periphery of the cap and distanced therefrom, the cap fitting being formed complementarily to the shell fitting for engaging the shell fitting; and a contact surface associated with the head for contacting the skin of a person.

5. The device of claim 4, wherein the contact surface is formed integrally with the cap.

6. The device of claim 5, wherein the contact surface includes a plurality of projections for gently scratching a person's back.

7. The device of claim 5, wherein the contact surface includes a plurality of holes, and the device further comprises a plurality of bristle tufts each anchored in a respective hole.

8. The device of claim 5, wherein the contact surface includes a plurality of protrusions, each having a gently contoured surface for massaging a person's skin when the protrusions are moved against the skin.

9. The device of claim 8, wherein the protrusions are formed integrally with the contact surface, and each protrusion defines a half-cylinder.

10. The device of claim 8, wherein the protrusions are rotatably mounted with respect to the contact surface, and each protrusion defines a cylinder.

11. The device of claim 4, further comprising a contact pad detachably engaged with the head, wherein the contact surface is established by the contact pad, and the contact pad is selected from the group of pads consisting of:

a hollow sponge pad having a continuous sponge contact surface and an opposed engagement surface formed with a slit therein, wherein a chamber for receiving the head is established between the surfaces of the sponge pad and the head can pass through the slit into the chamber to hold the sponge pad on the head;

a knitted single piece exfoliator pad having a polypropylene contact surface and defining a periphery for receiving the head therethrough to hold the knitted single piece exfoliator pad onto the head;

an exfoliator pad having a nylon or polypropylene net and an elastic sleeve fixedly attached to the nylon net, wherein the elastic sleeve is positionable over the head to hold the nylon net exfoliator pad onto the head; and a loofah attachment pad having a sponge-backed loofah contact surface and a skirt positionable over the head to hold the loofah attachment pad onto the head.

12. An applicator device for moving a contact surface against a person's back, comprising:

an elongated handle;

a generally disc-shaped shell formed on one end of the handle; and a generally disc-shaped cap detachably threadably engaged with the shell and operably associated with the contact surface;

wherein the shell defines a periphery and is formed with a threaded shell fitting centrally located relative to the periphery of the shell and distanced therefrom, and the cap defines a periphery and is formed with a threaded cap fitting centrally located relative to the periphery of the cap and distanced therefrom, the cap fitting being formed complementarily to the shell fitting for engaging the shell fitting.

13. The applicator device of claim 12, further comprising a contact surface formed integrally with the cap.

14. The applicator device of claim 13, wherein the contact surface includes a plurality of projections for gently scratching a person's back.

15. The applicator device of claim 13, wherein the contact surface include a plurality of holes, and the device further comprises a plurality of bristle tufts each anchored in a respective hole.

16. The applicator device of claim 13, wherein the contact surface includes a plurality of protrusions, each having a gently contoured surface for massaging a person's skin when the protrusions are moved against the skin.

17. The applicator device of claim 16, wherein the protrusions are formed integrally with the contact surface, and each protrusion defines a half-cylinder.

18. The applicator device of claim 16, wherein the protrusions are rotatably mounted with respect to the contact surface, and each protrusion defines a cylinder.

19. The applicator device of claim 12, further comprising a contact pad detachably engaged with the cap and establishing a contact surface, the contact pad being selected from the group of pads consisting of:

a hollow sponge pad having a continuous sponge contact surface and an opposed engagement surface formed with a slit therein, wherein a chamber for receiving the cap is established between the surfaces of the sponge pad and the cap can pass through the slit into the chamber to hold the sponge pad on the cap;

a knitted single piece exfoliator pad having a polypropylene contact surface and defining a periphery for receiving the cap therethrough to hold the knitted single piece exfoliator pad onto the cap;

an exfoliator pad having a nylon or polypropylene net and an elastic sleeve fixedly attached to the nylon net, wherein the elastic sleeve is positionable over the cap to hold the nylon net exfoliator pad onto the cap; and a loofah attachment pad having a sponge-backed loofah contact surface and a skirt positionable over the cap to, hold the loofah attachment pad onto the cap.

20. An applicator device, comprising:

an elongated curved shaft having a first end and a second end, the shaft including a manually grippable segment formed adjacent the first end of the shaft;

an applicator head formed on the second end of the shaft; and a plurality of contact pads, each individually engageable with the head, the contact pads including:

a hollow sponge pad having a continuous sponge contact surface and an opposed engagement surface formed with a slit therein, wherein a chamber for receiving the head is established between the surfaces of the sponge pad and the head can pass through the slit into the chamber to hold the sponge pad on the head;

a knitted single piece exfoliator pad having a polypropylene contact surface and defining a periphery for receiving the head therethrough to hold the knitted single piece exfoliator pad onto the head;

a nylon net exfoliator pad having a nylon net and an elastic sleeve fixedly attached to the nylon net, wherein the elastic sleeve is positionable over the head to hold the nylon net exfoliator pad onto the head; and a loofah attachment pad having a sponge-backed loofah contact surface and a skirt positionable over the head to hold the loofah attachment pad onto the head.

* * * * *